United States Patent
Choi et al.

(10) Patent No.: US 11,759,428 B2
(45) Date of Patent: *Sep. 19, 2023

(54) PHARMACEUTICAL FORMULATION COMPRISING ESOMEPRAZOLE AND SODIUM BICARBONATE

(71) Applicant: CHONG KUN DANG PHARMACEUTICAL CORP., Seoul (KR)

(72) Inventors: Jong Seo Choi, Yongin-Si (KR); Min Soo Kim, Yongin-Si (KR); Shin Jung Park, Yongin-Si (KR); Jong Lae Lim, Yongin-Si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/965,726

(22) PCT Filed: Jan. 28, 2019

(86) PCT No.: PCT/KR2019/001183
§ 371 (c)(1),
(2) Date: Jul. 29, 2020

(87) PCT Pub. No.: WO2019/147094
PCT Pub. Date: Aug. 1, 2019

(65) Prior Publication Data
US 2021/0030687 A1    Feb. 4, 2021

(30) Foreign Application Priority Data
Jan. 29, 2018    (KR) ................ 10-2018-0010987

(51) Int. Cl.
| | | |
|---|---|---|
| *A61K 9/28* | (2006.01) | |
| *A61K 9/20* | (2006.01) | |
| *A61K 31/4439* | (2006.01) | |
| *A61K 33/10* | (2006.01) | |

(52) U.S. Cl.
CPC .......... *A61K 9/2886* (2013.01); *A61K 9/2095* (2013.01); *A61K 9/284* (2013.01); *A61K 9/2893* (2013.01); *A61K 31/4439* (2013.01); *A61K 33/10* (2013.01)

(58) Field of Classification Search
CPC .... A61K 9/2886; A61K 9/2095; A61K 9/284; A61K 9/2893; A61K 31/4439; A61K 33/10
See application file for complete search history.

(56) References Cited

U.S. PATENT DOCUMENTS

| | | |
|---|---|---|
| 6,183,776 B1 | 2/2001 | Depui et al. |
| 6,369,085 B1 | 4/2002 | Cotton et al. |
| 2005/0239845 A1* | 10/2005 | Proehl .................. A61K 31/445 514/338 |
| 2005/0266071 A1 | 12/2005 | Olmstead et al. |
| 2007/0053981 A1* | 3/2007 | Blychert .............. A61K 9/0056 424/470 |
| 2009/0092658 A1 | 4/2009 | Hall et al. |
| 2010/0029654 A1 | 2/2010 | Pasinetti |
| 2012/0121664 A1 | 5/2012 | Pettersson et al. |
| 2012/0128764 A1 | 5/2012 | Venkatesh et al. |
| 2014/0271853 A1 | 9/2014 | Hall et al. |
| 2015/0044303 A1 | 2/2015 | Olmstead et al. |
| 2021/0030786 A1 | 2/2021 | Choi et al. |
| 2022/0233514 A1 | 7/2022 | Choi et al. |

FOREIGN PATENT DOCUMENTS

| | | | |
|---|---|---|---|
| CN | 1183047 A | 5/1998 | |
| CN | 101002769 A | 7/2007 | |
| CN | 101036633 A | 9/2007 | |
| CN | 102078616 A | 6/2011 | |
| CN | 102397277 A | 4/2012 | |
| CN | 103599082 A | 2/2014 | |
| CN | 103784414 A | 5/2014 | |
| CN | 103845734 A | 6/2014 | |
| CN | 103860584 A | 6/2014 | |
| CN | 103006691 B | 10/2014 | |
| CN | 104523746 A | 4/2015 | |
| CN | 204428461 U | 7/2015 | |
| EP | 0496437 A2 | 7/1992 | |
| EP | 3236952 B1 * | 7/2019 | ............. A61K 9/209 |
| JP | H11501950 A | 2/1999 | |
| JP | 2003-073270 A | 3/2003 | |

(Continued)

OTHER PUBLICATIONS

International Search Report for PCT Application No. PCT/KR2020/009250, dated Oct. 15, 2020.
Xingguo, "Microcarrier Drug Delivery System", Wuhan, Huazhong University of Science and Technology Press, 4 pages (2009) (English translation).
Xingguo, "Microcarrier Drug Delivery System", Wuhan, Huazhong University of Science and Technology Press, 4 pages (2009).
"Study Comparing Esomeprazole Associated With Sodium Bicarbonate From Eurofarma and Esomprazole in treatment of Gastroesophageal Reflux Disease ESOBIC," ClinicalTrials Identifier: NCT01471925 (2015).

(Continued)

*Primary Examiner* — Robert A Wax
*Assistant Examiner* — Olga V. Tcherkasskaya
(74) *Attorney, Agent, or Firm* — Foley Hoag LLP; David P. Halstead; Benjamin A. Vaughan

(57) ABSTRACT

The present invention relates to a stable pharmaceutical formulation comprising omeprazole, its enantiomer, or its pharmaceutically acceptable salt, and sodium bicarbonate, and a method for preparing the same. Specifically, the present invention provides a stable formulation by preventing omeprazole, its enantiomer, or its pharmaceutically acceptable salt, from coming in direct contact with sodium bicarbonate, to reduce the production of impurities.

7 Claims, No Drawings

(56) References Cited

FOREIGN PATENT DOCUMENTS

| | | |
|---|---|---|
| JP | 2006/505566 A | 2/2006 |
| JP | 2006-528198 A | 12/2006 |
| JP | 2007526319 A | 9/2007 |
| JP | 2008/500365 A | 1/2008 |
| JP | 2008-504372 A | 2/2008 |
| JP | 2008-512453 A | 4/2008 |
| JP | 2009534441 A | 9/2009 |
| JP | 2011-512416 A | 4/2011 |
| JP | 2011530569 A | 12/2011 |
| JP | 2016-509061 A | 3/2016 |
| JP | 7003279 B2 | 1/2022 |
| KR | 10-0115254 B | 12/1995 |
| KR | 960003605 B1 | 3/1996 |
| KR | 100274698 B1 | 12/2000 |
| KR | 10-2002-0089322 A | 11/2002 |
| KR | 100384960 B1 | 8/2003 |
| KR | 10-2004-0047771 A | 6/2004 |
| KR | 10-2004-0099265 A | 11/2004 |
| KR | 2005/0061647 A | 6/2005 |
| KR | 100679767 B1 | 2/2007 |
| KR | 10-2010-0066742 A | 6/2010 |
| KR | 10-2011-0079641 A | 7/2011 |
| KR | 10-2011-0123178 A | 11/2011 |
| KR | 101104349 B1 | 1/2012 |
| KR | 20130115593 A | 10/2013 |
| KR | 10-2015-0083255 A | 7/2015 |
| KR | 20160020625 A | 2/2016 |
| KR | 10-2016-0082169 A | 7/2016 |
| KR | 10-2016-0124368 A | 10/2016 |
| KR | 2017/0076494 A | 7/2017 |
| KR | 10-2017-0126915 A | 11/2017 |
| KR | 10-2017-0136771 A | 12/2017 |
| KR | 20180011624 A | 2/2018 |
| KR | 20180098744 A | 9/2018 |
| KR | 20190003312 A | 1/2019 |
| KR | 20190037182 A | 4/2019 |
| KR | 10-2006777 | 10/2019 |
| KR | 10-2080023 B1 | 2/2020 |
| KR | 10-2146395 | 8/2020 |
| WO | WO-2001/051050 A1 | 7/2001 |
| WO | WO-2003/009846 A1 | 2/2003 |
| WO | WO-2005/092297 A2 | 10/2005 |
| WO | WO-2008110070 A1 | 9/2008 |
| WO | WO-2016/024822 A1 | 2/2016 |
| WO | WO-2017/122212 A1 | 7/2017 |
| WO | WO-2019/146937 A1 | 8/2019 |
| WO | WO-2019/147094 A1 | 8/2019 |
| WO | WO-2020/040438 A1 | 2/2020 |

OTHER PUBLICATIONS

Approval package NDA21153S-008 (Astrazeneca, Jan. 9, 04).
Howden., "Immediate-Release Omeprazole/Sodium Bicarbonate," Gastroenterology & Hepatology, 2(5): 386 (2006).
International Search Report for PCT Application No. PCT/KR2019/009371 dated Oct. 25, 2019.
Gardner et al., "Integrated Acidity and the Pathophysiology of Gastroesophageal Reflux Disease", The American Journal of Gastroenterology, vol. 96, No. 5, 2001, pp. 1363-1370.
Information Sheet on Esoduo Tabs 20/800 mg, permit date Apr. 30, 2018, with English machine translation.
Information Sheet on Ganaflux Tab 40/1100 mg, date of approval Jun. 19, 2015 (with partial English translation).
Kim et al. "The safety, pharmacodynamics, and pharmacokinetics of immediate-release formulation containing esomeprazole 20 mg/sodium bicarbonate 800 mg in healthy adult male", Drug Design, Development and Therapy 2019:13, pp. 3151-3159.
Lee et al., "Effect of Other Medications on the Stability of Omeprazole in Aqueous Solution for the Peptic Ulcer Disease", Journal of the Korean Society of Industrial Science and Technology, vol. 10, No. 11, pp. 3494-3499, 2009 (with English abstract).
Mishra et al. "Formulation, Development and Evaluation of an Immediate Release Buffer Tablet of Omeprazole", Pharma Science Monitor 7(2), Apr.-Jun. 2016, pp. 270-281.
Newspaper Article from MedicalObserver.com describing Eso Duo Tab, dated Jul. 23, 2018, updated Mar. 24, 2021 (with partial English translation).
Newspaper Article from MedicalTimes.com describing Chong Kun Dang combination of esomeprazole and sodium bicarbonate, dated Jan. 26, 2018, accessed Mar. 26, 2021 (with partial English translation).
Newspaper Article from Yakup.com describing Ganaflux Tab (40-1100 mg), accessed Mar. 26, 2021 (with partial English translation).
Tutuian et al., "The acidity index: a simple approach to the measurement of gas acidity", Aliment Pharmacol Ther 2004; 19: pp. 443-448.
Yacyshyn et al., "The Clinical Importance of Proton Pump Inhibitor Pharmacokinetics", Digestion 2002; 66: pp. 67-78.
Levina et al., "The Influence of Film Coatings on Performance of Hypromellose Matrices", published by Colorcon, dated Feb. 5, 2020, 3 pages.
Protocol for Testing and Analysis of Nexoduo tablet 20/80mg, dated Oct. 5, 2021 (with English translation), 3 pages.
Rowe et al., "Handbook of Pharmaceutical Excipients" Sixth Edition, Pharmaceutical Press, published 2009.
Certificate of Analysis for Opadry Amb II High Performance Moisture Barrier Film Coating 88A5400358 Pink, dated Mar. 30, 2020, 6 pages.

* cited by examiner

PHARMACEUTICAL FORMULATION COMPRISING ESOMEPRAZOLE AND SODIUM BICARBONATE

RELATED APPLICATIONS

This application is the U.S. National Phase of International Patent Application No. PCT/KR2019/001183, filed Jan. 28, 2019, which claims the benefit of priority to Korean Patent Application No. KR 10-2018-0010987, filed Jan. 29, 2018. International Patent Application No. PCT/KR2019/001183 is incorporated herein by reference in its entirety.

TECHNICAL FIELD

The present invention relates to a stable pharmaceutical formulation comprising omeprazole, its enantiomer, or its pharmaceutically acceptable salt, and sodium bicarbonate, and the method for preparing the same. Specifically, the present invention provides a stable formulation by preventing omeprazole, its enantiomer, or its pharmaceutically acceptable salt from coming in direct contact with sodium bicarbonate, to reduce the production of impurities.

BACKGROUND ART

Omeprazole has a chemical name of 5-methoxy-2-[(4-methoxy-3,5-dimethyl-2-pyridinyl)methyl]sulfinyl-1H-benzimidazol. Omeprazole exists in the two types of isomers: R-isomer and S-isomer. S-isomer is known for being remarkably excellent in terms of the treatment effect and side effects in comparison with R-isomer. S-isomer refers to (S)-5-methoxy-2-[(4-methoxy-3,5-dimethyl-2-pyridinyl)-methyl]sulfinyl-1H-benzimid azol, which is commonly called esomeprazole.

Esomeprazole is a representative proton-pump inhibitor (PPI) which is used for the treatment of dyspepsia, peptic ulcer disease, gastroesophageal reflux disease, Zollinger-Ellison syndrome, and the like.

It is well known in the art that omeprazole, especially, esomeprazole, is prone to degradation or transformation in acidic and neutral media. More particularly, esomeprazole is known to have less than 10 minutes of a degradation half-life in an aqueous solution having 3 or lower of pH. As such, decomposition of esomeprazole is catalyzed by an acidic compound, and also affected by moisture, heat, organic solvents, and light.

Thus, there have been a lot of demands on a stable esomeprazole formulation. In order to solve the stability issue, Korean Patent No. 384960 discloses a method of preparing a pellet comprising a magnesium salt of esomeprazole, followed by enteric coating, adding excipients, and formulating as a tablet. The formulation as prepared based on the method described above is currently being marketed under the trade name of Nexium®.

However, an enteric-coated tablet such as Nexium® is not suitable for the treatment of diseases requiring immediate therapeutic effect after administration, such as gastric acid-related diseases, because it was designed to be dissolved and absorbed in the intestine while not causing immediate absorption in the stomach.

Korean Patent No. 1104349 discloses an enteric-coated tablet and capsule wherein the insufficiency of the stability and properties of omeprazole was improved by preparing a solid dispersion formulation with magnesium oxide and povidone.

Korean Patent Publication No. 10-1996-0003605 discloses a method for preparing a solid dispersion formulation comprising omeprazole as an active ingredient wherein beta-cyclodextrin and sodium hydroxide are added as a stabilizing ingredient. However, the invention as described in the above undesirably uses sodium hydroxide which is harmful to human body. The process of preparing the solid dispersion comprises dissolving the active ingredient, omeprazole, in a solvent, wherein a special stabilizer such as sodium hydroxide is required to stabilize omeprazole.

To solve these problems, Korean Patent No. 679767 discloses a method of using a buffering agent such as sodium bicarbonate for omeprazole.

However, the use of a large amount of sodium bicarbonate has the disadvantage of reducing the efficacy of omeprazole and causing side effects. In particular, when sodium bicarbonate is administered in a large amount, the stomach may be swollen to further increase pain in a critical patient. The absorption of sodium bicarbonate may induce burping while the burping may cause gastric acid to move upward, whereby deteriorating gastroesophageal reflux disease. Further, patients with symptoms such as hypertension or heart failure should avoid the intake of sodium which may result in hypertensive symptoms. As such, it is not appropriate to administer a large amount of sodium bicarbonate to patients with these symptoms. In addition, the administration of a large amount of sodium bicarbonate to patients with various complications is at risk of causing metabolic alkalemia. Moreover, because buffering agents that alter pH of the stomach and urine may affect an absorption, distribution, and metabolic process of a drug, the use of a large amount of sodium bicarbonate with omeprazole requires more attention.

Further, since the compatibility between omeprazole or its enantiomer, and sodium bicarbonate is not good, contacting each other may cause increased impurities.

DISCLOSURE OF INVENTION

Technical Problem

The inventors have developed a formulation comprising sodium bicarbonate as an antacid that increases intragastric pH so as to stabilize omeprazole or its enantiomer which is unstable at a low pH. However, in order to solve the problem of the compatibility that may be caused by simultaneously comprising omeprazole or its enantiomer and sodium bicarbonate, we tried to apply different coating agents through the experiments and research for a long period to confirm that polyvinyl alcohol is most appropriate, based on which the present invention was achieved.

It was also confirmed that polyvinyl alcohol not only prevents omeprazole or its enantiomer from coming in contact with sodium bicarbonate to improve stability of a formulation, but also is used for coating the outer part of a tablet to further enhance stability of a formulation. As such, a formulation having very improved stability has been developed.

Solution to Problem

The present invention relates to a pharmaceutical formulation comprising omeprazole, its enantiomer, or its pharmaceutically acceptable salt, and sodium bicarbonate, and further comprising polyvinyl alcohol as a coating agent.

Omeprazole may be in any enantiomer type of S-isomer or R-isomer, preferably, S-isomer, i.e., esomeprazole.

The term "a pharmaceutically acceptable salt" as used herein may be, but is not limited to, a metal salt comprising sodium, potassium, calcium, magnesium, zinc, lithium, etc., or an ammonium salt. Among them, a magnesium salt is preferable.

Omeprazole, its enantiomer, or its pharmaceutically acceptable salt may be in a solvate comprising hydrates such as monohydrate, dihydrate, or trihydrate, and may be in an amorphous or crystal form.

Sodium bicarbonate may be used as an antacid to stabilize omeprazole or its enantiomer that is unstable at a low pH.

The coating agent according to the present invention separates and/or prevents omeprazole, its enantiomer, or its pharmaceutically acceptable salt from coming in direct contact with sodium bicarbonate, so that it plays a role in improving compatibility.

The present invention relates to a pharmaceutical formulation, characterized in comprising the first layer comprising omeprazole, its enantiomer, or its pharmaceutically acceptable salt; the second layer comprising polyvinyl alcohol as a coating agent; and the third layer comprising sodium bicarbonate as an antacid.

Further, the coating agent according to the present invention is used for coating the outer part of a formulation, so that it plays a role in improving stability.

Further, the present invention relates to a pharmaceutical formulation further comprising the fourth layer comprising polyvinyl alcohol as a coating agent.

The coating agent in the above second and fourth layers may be comprised in 0.1 to 7 parts by weight, preferably, 0.5 to 5 parts by weight based on 1 part by weight of omeprazole, its enantiomer, or its pharmaceutically acceptable salt.

A pharmaceutical formulation according to the present invention may be prepared based the following steps:

first coating a core with a coating solution comprising omeprazole, its enantiomer, or its pharmaceutically acceptable salt to prepare a first coated material;

coating the first coated material with a second coating solution comprising polyvinyl alcohol to prepare a second coated material;

tableting the second coated material with sodium bicarbonate to prepare a core tablet; and coating the core tablet with a third coating solution comprising polyvinyl alcohol.

More Specifically, the present invention relates to a pharmaceutical formulation comprising 20 mg or 40 mg of esomeprazole magnesium trihydrate based on the weight of esomeprazole, and 800 mg of sodium bicarbonate, which may be prepared based on the following steps:

first coating a core with a coating solution comprising esomeprazole magnesium trihydrate to prepare a first coated material;

coating the first coated material with a second coating solution comprising polyvinyl alcohol to prepare a second coated material;

tableting the second coated material with sodium bicarbonate to prepare a core tablet; and coating the core tablet with a third coating solution comprising polyvinyl alcohol.

Advantageous Effects of Invention

The present invention relates to a pharmaceutical formulation with improved stability, comprising omeprazole, its enantiomer, or its pharmaceutically acceptable salt, and sodium bicarbonate. In the pharmaceutical formulation according to the present invention, omeprazole is prevented from coming in contacting with sodium bicarbonate to improve compatibility, while a tableted tablet is coated to further improve stability.

The formulation according to the present invention is prepared in a monolayered tablet, which results in easy preparation and improved stability. Further, the formulation is immediately dissolved and absorbed in the stomach to have improved dissolution rate and bioavailability.

MODE FOR THE INVENTION

Hereinafter, the present invention will be more detailed through the following examples. However, the examples are merely provided for a better understanding of the present invention for the purpose of illustration, but are not to be construed as the limitation of the claimed scope.

Example 1

Preparation of a Tablet of Esomeprazole Comprising PVA (Polyvinyl Alcohol) as a Coating Agent A tablet of esomeprazole comprising PVA was prepared based on the method as follows.

1. First Coating

Hydroxypropyl cellulose was added and dissolved in purified water, followed by adding arginine, simethicone, purified water, esomeprazole magnesium trihydrate (22.3 mg; 20.00 mg based on the weight of esomeprazole), magnesium oxide, and talc, and dispersing them, to prepare a coating solution. Sugar spheres were put into a fluidized bed granulation-coating machine, spraying the coating solution, to prepare a first coated material.

2. Second Coating

Polyvinyl alcohol (7.4 mg; 0.7 wt % based on the total weight of the tablet), talc, titanium oxide, glycerol monocaprylocaprate, and sodium lauryl sulfate were added and dispersed in purified water to prepare a coating solution. The first coated materials from the first coating process were put into a fluidized bed granulation-coating machine, spraying the coating solution, to prepare a second coated material.

3. Blending and Tableting [50] The second coated material, sodium bicarbonate (800 mg), copovidone, and crospovidone were put in a mixer to be blended, followed by adding sodium stearyl fumarate and lubricating to prepare granules. The prepared granules were tableted.

4. Third Coating

Polyvinyl alcohol (15.5 mg; 1.5 wt % based on the total weight of the tablet), talc, titanium oxide, glycerol monocaprylocaprate, sodium lauryl sulfate, red iron oxide, black iron oxide, and yellow iron oxide were added in purified water to prepare a coating solution. The core tablets were put into a coating machine, spraying the coating solution, coating, and drying to obtain the final film coated tablet.

Comparative Example 1

Preparation of a Tablet of Esomeprazole Comprising Hydroxypropyl Methylcellulose as a Coating Agent The tablet was prepared based on the following method, provided that hydroxypropyl methylcellulose was used as a coating agent for the second and third coating steps, instead of polyvinyl alcohol used in Example 1.

1. First Coating

Hydroxypropyl cellulose was added and dissolved in purified water, followed by adding simethicone, esomeprazole magnesium trihydrate, magnesium oxide, talc, polyethylene glycol, and Tween80 and dispersing them, to prepare a coating solution. Sugar spheres were put into a fluidized bed granulation-coating machine, spraying the coating solution, to prepare a first coated material.

2. Second Coating

Hydroxypropyl methylcellulose, polyethylene glycol, sodium hydroxide, simethicone, and talc were added and dissolved in purified water to prepare a coating solution. The first coated materials were put into a fluidized bed granulation-coating machine, spraying the coating solution to prepare a second coated material.

3. Blending and Tableting

The second coated material, sodium bicarbonate, copovidone, and crospovidone were added in a mixer to be blended, followed by adding sodium stearyl fumarate to prepare granules. The granules were tableted.

4. Third Coating

Hydroxypropyl methylcellulose, titanium oxide, talc, polyethylene glycol, yellow iron oxide, red iron oxide, and black iron oxide were added in purified water to prepare a coating solution. The core tablets were put into a coating machine, spraying the coating solution, coating, and drying to obtain the final film coated tablet.

Comparative Examples 2 and 3

Preparation of a Tablet of Esomeprazole Comprising Hydroxypropyl Methylcellulose (HPMC) or Polyvinyl Alcohol (PVA) as a Coating Agent The tablets of Comparative Examples 2 and 3 were prepared based on the method for preparing a tablet provided in Example 1, provided that Comparative Examples 2 and 3 used HPMC, instead of PVA, as a second coating agent and a third coating agent, respectively.

The type of coating agent used in the preparation of Example 1 and Comparative Examples 1 to 3 are shown in Tablet 1 below.

TABLE 1

| | Second coating agent | Third coating agent |
|---|---|---|
| Example 1 | PVA | PVA |
| Comparative Example 1 | HPMC | HPMC |
| Comparative Example 2 | HPMC | PVA |
| Comparative Example 3 | PVA | HPMC |

Test Example 1

Impurities Test

Stability test on the tablets of Example 1 and Comparative Examples 1 to 3 was carried out at accelerated conditions. The amount of impurities was measured by using the analytical condition below.

<Analytical Condition>

1) Detector: UV spectrophotometer (measurement wavelength: 305 nm)
2) Column: Phenomenex Luna $C_{18}$ (4.6×150 mm, 3 μm) or equivalent column
3) Injection volume: 50 μL
4) Flow rate: 1.0 mL/min
5) Column temperature: Constant temperature near 30° C.
6) Sample temperature: Constant temperature near 4° C.
7) Mobile phase:

Mobile phase A—A solution where a mixture liquid of buffer solution at pH 8.7, acetonitrile, and methanol (7:2:1) was adjusted to have pH 8.7 with n-butylamine Mobile phase B—Buffer solution at pH 8.7 and acetonitrile (2:8)

| Time (min) | Mobile phase A | Mobile phase B |
|---|---|---|
| 0 | 100 | 0 |
| 20 | 100 | 0 |
| 25 | 70 | 30 |
| 35 | 80 | 20 |
| 40 | 80 | 20 |
| 45 | 100 | 0 |
| 50 | 100 | 0 |

The buffer solution at pH 8.7 was prepared as follows: 0.71 g of sodium perchlorate ($NaClO_4$) and 5 mL of n-butylamine were taken to be put in an 1 L volumetric flask, followed by filling the flask with purified water up to the calibration mark and adjusting the pH to 8.7 with perchloric acid.

The test results of impurities were shown in Tables 2 to 4 below.

TABLE 2

Amount of omeprazole sulfone (Specification: not more than 0.5%)

| | Initial state | 1 month at accelerated conditions | 3 months at accelerated conditions |
|---|---|---|---|
| Example 1 | 0.08% | 0.11% | 0.15% |
| Comparative Example 1 | 0.10% | 0.19% | 0.39% |
| Comparative Example 2 | 0.10% | 0.15% | 0.29% |
| Comparative Example 3 | 0.10% | 0.15% | 0.29% |

As shown in Table 2 above, it was confirmed that the tablet of Example 1 had the smallest amount of omeprazole sulfone, and thus was most stable. In case of 3 months at accelerated conditions, Comparative Examples 1 to 3 had 2 times more of the impurities amount of omeprazole sulfone than Example 1.

Further, Comparative Example 1 using HPMC, instead of PVA, as a coating agent in both the second and third layers showed low stability to Comparative Examples 2 and 3 using PVA as a coating agent in either one of the second or third layer.

TABLE 3

Amount of individual unknown impurities (Specification: not more than 0.2%)

| | Initial state | 1 month at accelerated conditions | 3 months at accelerated conditions |
|---|---|---|---|
| Example 1 | 0.01% | 0.05% | 0.10% |
| Comparative Example 1 | 0.09% | 0.24% | 0.51% |
| Comparative Example 2 | 0.06% | 0.19% | 0.32% |
| Comparative Example 3 | 0.06% | 0.19% | 0.32% |

As shown in Table 3 above, it was confirmed that the tablet of Example 1 had the smallest amount of individual unknown impurities, and thus was most stable. In case of 1 month and 3 months at accelerated conditions, Comparative Examples 1 to 3 had almost 3 to 5 times more of the amount of individual unknown impurities than Example 1. In case of 3 months at accelerated conditions, the amount of impurities in Comparative Examples 1 to 3 was over the specification of 0.2%, which means that the results of stability test did not met the acceptance criteria.

Further, Comparative Example 1 using HPMC, instead of PVA, as a coating agent in both the second and third layers showed inferior stability to Comparative Examples 2 and 3 using PVA as a coating agent in either one of the second or third layer.

TABLE 4

| | Amount of total impurities (Specification: not more than 2.0%) | | |
|---|---|---|---|
| | Initial state | 1 month at accelerated condition | 3 months at accelerated conditions |
| Example 1 | 0.04% | 0.32% | 0.87% |
| Comparative Example 1 | 0.29% | 1.08% | 1.11% |
| Comparative Example 2 | 0.19% | 0.58% | 1.33% |
| Comparative Example 3 | 0.19% | 0.58% | 1.33% |

As shown in Table 4 above, it was confirmed that the tablet of Example 1 had the smallest amount of the total impurities, and thus was most stable.

In conclusion, it was confirmed that the tablet of Example 1 exerts remarkably improved stability in the amount of individual unknown impurities and total impurities, in comparison with the tablets of Comparative Examples 1 to 3.

Further, the most improved stability was obtained when using polyvinyl alcohol as a coating agent for preventing the contact between omeprazole and sodium bicarbonate, and also using polyvinyl alcohol as a coating agent for coating the outer part of a tablet.

The invention claimed is:

1. A pharmaceutical formulation comprising a first layer, a second layer, a third layer, and a fourth layer;
   the first layer comprising omeprazole, its enantiomer, or its pharmaceutically acceptable salt;
   the second layer comprising a coating agent, wherein the coating agent is polyvinyl alcohol;
   the third layer comprising an antacid, wherein the antacid is sodium bicarbonate; and
   the fourth layer comprising a coating agent, wherein the coating agent is polyvinyl alcohol;
   wherein the second layer separates the first layer from the third layer.

2. The pharmaceutical formulation according to claim 1, wherein the ratio of the coating agent in the second and fourth layers to the omeprazole, its enantiomer, or its pharmaceutically acceptable salt, is from 0.1:1 to 7:1 by weight.

3. The pharmaceutical formulation according to claim 2, wherein the ratio of the coating agent in the second and fourth layers to the omeprazole, its enantiomer, or its pharmaceutically acceptable salt, is from 1.5:1 to 5:1 by weight.

4. The pharmaceutical formulation according to claim 1, wherein the omeprazole, its enantiomer, or its pharmaceutically acceptable salt is esomeprazole.

5. The pharmaceutical formulation according to claim 1, wherein the omeprazole, its enantiomer, or its pharmaceutically acceptable salt is a magnesium salt of esomeprazole.

6. A method for preparing a pharmaceutical formulation comprising omeprazole, its enantiomer, or its pharmaceutically acceptable salt; and sodium bicarbonate, the method comprising the steps:
   coating a core with a coating solution comprising omeprazole, its enantiomer, or its pharmaceutically acceptable salt to prepare a first coated material;
   coating the first coated material with a second coating solution comprising polyvinyl alcohol to prepare a second coated material;
   tableting the second coated material with sodium bicarbonate to prepare a core tablet; and
   coating the core tablet with a third coating solution comprising polyvinyl alcohol.

7. A method for preparing a pharmaceutical formulation comprising 20 mg or 40 mg of esomeprazole magnesium trihydrate based on the weight of esomeprazole, and 800 mg of sodium bicarbonate, the method comprising the steps:
   coating a core with a coating solution comprising esomeprazole magnesium trihydrate to prepare a first coated material;
   coating the first coated material with a second coating solution comprising polyvinyl alcohol to prepare a second coated material;
   tableting the second coated material with sodium bicarbonate to prepare a core tablet; and
   coating the core tablet with a third coating solution comprising polyvinyl alcohol.

\* \* \* \* \*